US012029883B2

(12) United States Patent
McKinnon

(10) Patent No.: US 12,029,883 B2
(45) Date of Patent: Jul. 9, 2024

(54) SYRINGE PUMP VIBRATION MODULE TO REDUCE STOPPER FRICTION

(71) Applicant: Becton, Dickinson and Company, Franklin Lakes, NJ (US)

(72) Inventor: Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 886 days.

(21) Appl. No.: 16/978,071

(22) PCT Filed: Mar. 19, 2019

(86) PCT No.: PCT/US2019/022976
§ 371 (c)(1),
(2) Date: Sep. 3, 2020

(87) PCT Pub. No.: WO2019/183098
PCT Pub. Date: Sep. 26, 2019

(65) Prior Publication Data
US 2021/0016012 A1  Jan. 21, 2021

Related U.S. Application Data

(60) Provisional application No. 62/645,423, filed on Mar. 20, 2018.

(51) Int. Cl.
*A61M 5/315* (2006.01)
*A61M 5/142* (2006.01)
*A61M 5/31* (2006.01)

(52) U.S. Cl.
CPC ........ *A61M 5/31513* (2013.01); *A61M 5/142* (2013.01); *A61M 5/3129* (2013.01); *A61M 5/31578* (2013.01); *A61M 2205/0294* (2013.01); *A61M 2205/3327* (2013.01); *A61M 2205/3331* (2013.01); *A61M 2205/52* (2013.01)

(58) Field of Classification Search
CPC .............. A61M 5/31513; A61M 5/142; A61M 5/3129; A61M 5/31578; A61M 2205/3331; A61M 2205/0294; A61M 2205/3327; A61M 2205/52; A61M 5/31; A61M 5/178
See application file for complete search history.

(56) References Cited

U.S. PATENT DOCUMENTS

| 5,647,851 A | 7/1997 | Pokras |
| 2003/0036725 A1 | 2/2003 | Lavi et al. |
| 2010/0204633 A1 | 8/2010 | Kopperschmidt |
| 2011/0148330 A1 | 6/2011 | Zhou |

(Continued)

FOREIGN PATENT DOCUMENTS

| CN | 101835504 A | 9/2010 |
| CN | 103458810 A | 12/2013 |

(Continued)

*Primary Examiner* — Theodore J Stigell
*Assistant Examiner* — Rachel T. Smith
(74) *Attorney, Agent, or Firm* — The Webb Law Firm

(57) ABSTRACT

A syringe assembly includes a syringe and a vibrator configured to vibrate at at least one frequency to reduce stopper friction. The vibrator is attached to the syringe. The syringe assembly may further include an infusion pump configured to draw fluid from the syringe with a negative pressure.

23 Claims, 11 Drawing Sheets

(56) References Cited

U.S. PATENT DOCUMENTS

| | | | | |
|---|---|---|---|---|
| 2012/0209303 A1* | 8/2012 | Frankhouser | ....... | A61M 5/3287 606/169 |
| 2013/0242082 A1* | 9/2013 | Miller | ................... | G06T 7/0004 348/94 |
| 2015/0367068 A1* | 12/2015 | Kawamura | ........... | A61M 5/172 604/67 |
| 2019/0133822 A1* | 5/2019 | Banko | ................... | A61M 1/774 |

FOREIGN PATENT DOCUMENTS

| | | | | |
|---|---|---|---|---|
| JP | 2004508897 A | 3/2004 | | |
| WO | 2008086560 A1 | 7/2008 | | |
| WO | WO-2008086560 A1 * | 7/2008 | ............ | A61M 5/422 |
| WO | 2012109621 A1 | 8/2012 | | |
| WO | 2014066937 A1 | 5/2014 | | |
| WO | WO-2014066937 A1 * | 5/2014 | ..... | A61B 17/320068 |
| WO | 2019081518 A1 | 5/2019 | | |

\* cited by examiner

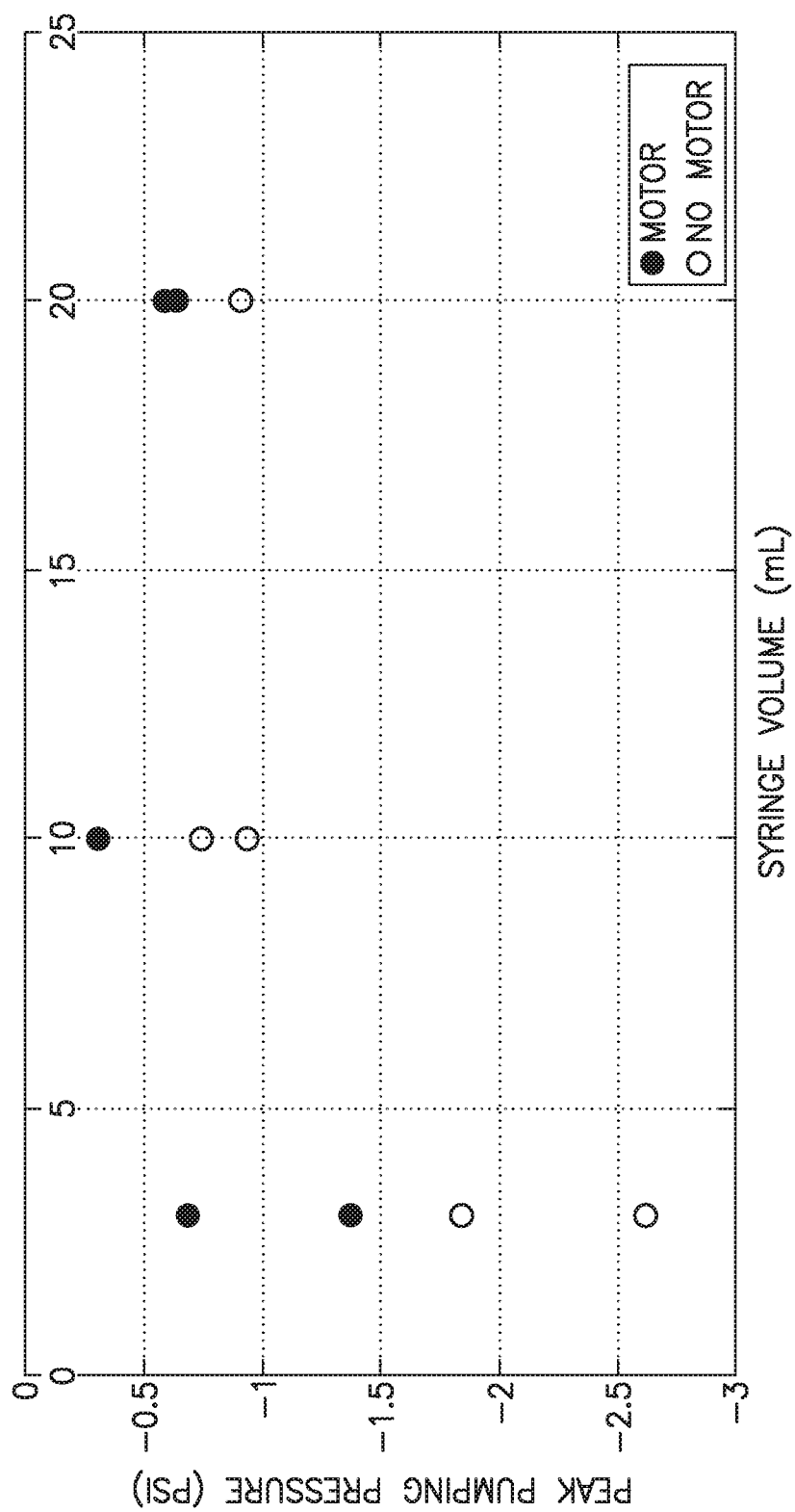

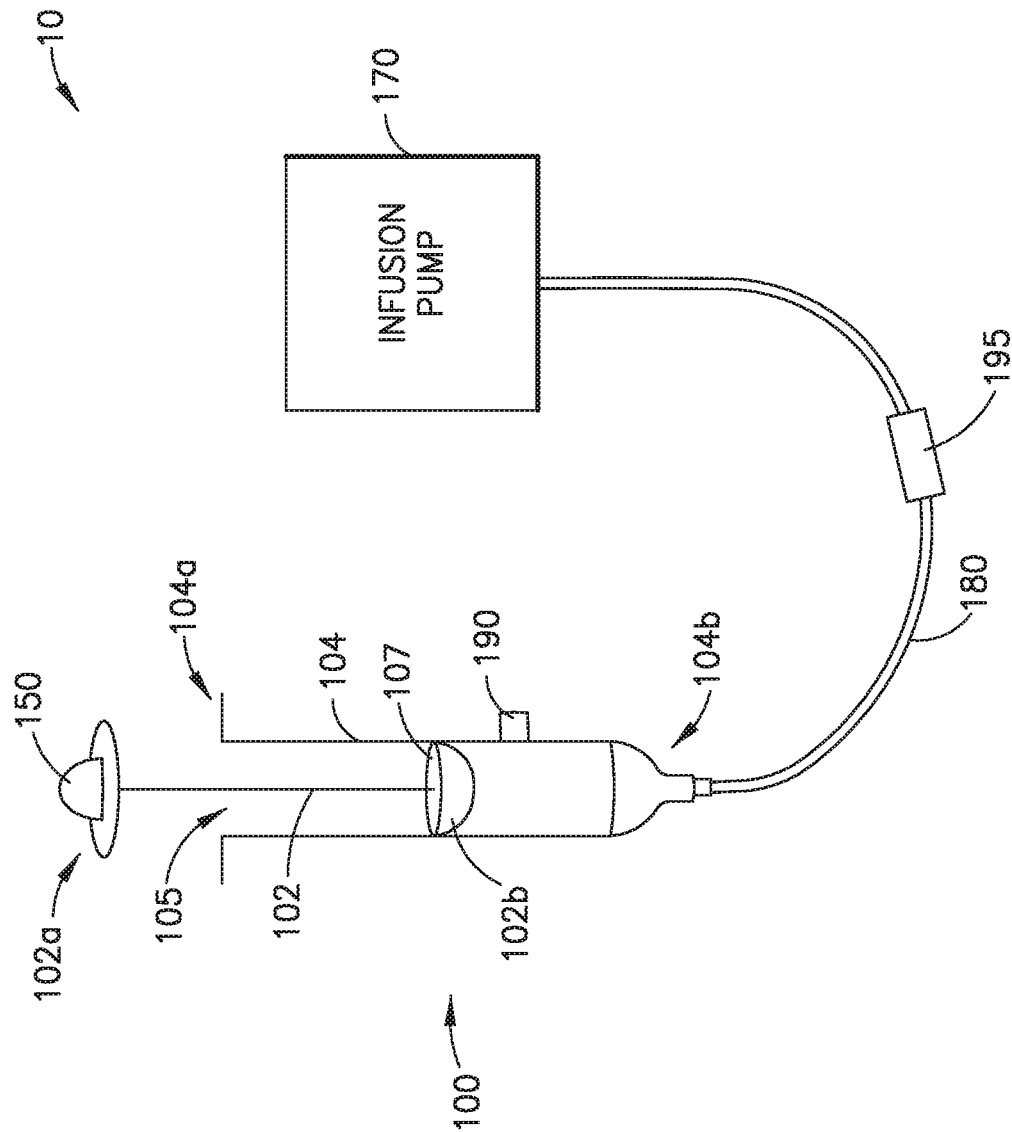

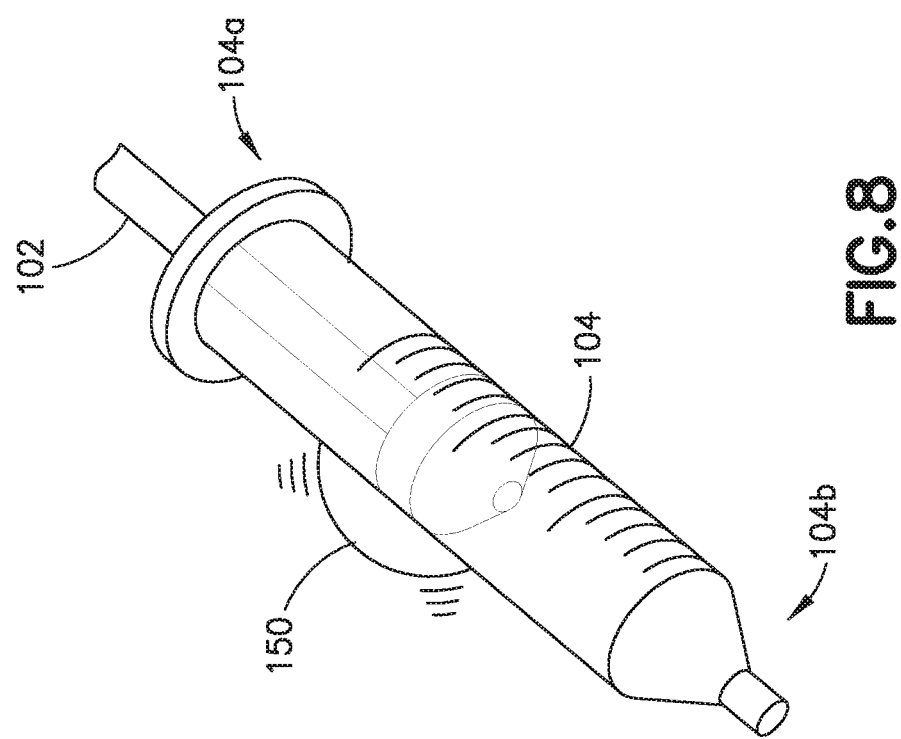

SYRINGE PUMP VIBRATION MODULE TO REDUCE STOPPER FRICTION

CROSS-REFERENCE TO RELATED APPLICATION

This application is the United States national phase of International Application No. PCT/US2019/022976 filed Mar. 19, 2019, and claims priority to U.S. Provisional Application Ser. No. 62/645,423, entitled "Syringe Pump Vibration Module to Reduce Stopper Friction", filed Mar. 20, 2018, the disclosures of which are hereby incorporated by reference in their entirety.

BACKGROUND

Field of the Invention

This invention relates generally to a syringe assembly and, more particularly, to a syringe assembly including a vibrator to reduce stopper friction during infusion.

Description of Related Art

Stiction is the static friction that needs to be overcome to enable relative motion of stationary objects in contact. Stiction arises in syringes between the stopper and the inner wall of the syringe barrel. Syringe stiction reduction has typically been considered for ergonomic reasons, but also because it introduces a noise factor into the accuracy of conventional syringe pumps. Stiction control or reduction is typically approached in the context of lubricants or stopper design.

For syringe pumps designed to draw from the tip of a syringe, rather than depressing the plunger, the negative pressure required to draw from smaller syringe sizes can become prohibitive for any pump. Conventional syringe pumps are not as susceptible to stiction related problems as these "draw-from-the-tip" pumps. Syringe break-loose force or stiction data illustrating the pressures required to draw from a range of syringe sizes is shown in FIG. 1.

Accordingly, there is a need in the art for improved solutions for reducing stiction and/or the negative pressure required to draw fluid from syringes.

SUMMARY

The present invention is directed to a syringe assembly that reduces stiction between the stopper and the inner wall of a syringe barrel and/or enables a reduction in the negative pressure required to draw from syringes in an inexpensive and robust manner.

According to one preferred and non-limiting embodiment or aspect, provided is a syringe assembly, comprising: a syringe; and a vibrator configured to vibrate at at least one frequency, wherein the vibrator is attached to the syringe.

In one preferred and non-limiting embodiment or aspect, the vibrator comprises one of an eccentric weight on a motor shaft, a piezoelectric drive, and an inductive drive.

In one preferred and non-limiting embodiment or aspect, the vibrator is configured to vibrate at a natural frequency of the syringe assembly.

In one preferred and non-limiting embodiment or aspect, the vibrator is configured to vibrate at a plurality of different frequencies.

In one preferred and non-limiting embodiment or aspect, the syringe assembly further comprises at least one sensor configured to determine a natural frequency of the syringe assembly.

In one preferred and non-limiting embodiment or aspect, the at least one sensor is configured to determine a dynamic response of the syringe assembly to the plurality of different frequencies and determine the natural frequency of the syringe assembly based on the dynamic response of the syringe assembly to the plurality of different frequencies.

In one preferred and non-limiting embodiment or aspect, the at least one sensor comprises an accelerometer.

In one preferred and non-limiting embodiment or aspect, the vibrator is configured to vibrate at the natural frequency of the syringe assembly determined by the at least one sensor.

In one preferred and non-limiting embodiment or aspect, the vibrator has a predetermined mass configured to tune the natural frequency of the syringe assembly to a preselected natural frequency.

In one preferred and non-limiting embodiment or aspect, the syringe comprises a plunger rod and a syringe barrel, and wherein the vibrator is attached to the plunger rod.

In one preferred and non-limiting embodiment or aspect, the syringe barrel extends between a proximal end and a distal end, wherein the proximal end of the syringe barrel is configured to receive a distal end of the plunger rod, and the wherein the vibrator is attached to a proximal end of the plunger rod.

In one preferred and non-limiting embodiment or aspect, the vibrator is configured to impute motion to the plunger rod in an axial direction of the syringe barrel.

In one preferred and non-limiting embodiment or aspect, the syringe barrel extends between a proximal end and a distal end, wherein the proximal end of the syringe barrel is configured to receive a distal end of the plunger rod, and wherein the vibrator is attached between a proximal end and the distal end of a plunger rod.

In one preferred and non-limiting embodiment or aspect, the vibrator is configured to impute motion to the plunger rod in a direction transverse to an axial direction of the syringe barrel.

In one preferred and non-limiting embodiment or aspect, the syringe comprises a plunger rod and a syringe barrel, and wherein the vibrator is attached to the syringe barrel.

In one preferred and non-limiting embodiment or aspect, the vibrator is configured to impute motion to the syringe barrel in a direction transverse to an axial direction of the syringe barrel.

In one preferred and non-limiting embodiment or aspect, the vibrator is removably attached to the syringe.

In one preferred and non-limiting embodiment or aspect, the vibrator is attached to the syringe by at least one of an adhesive connection, a mechanical connection, and a magnetic connection.

In one preferred and non-limiting embodiment or aspect, the syringe assembly further comprises an infusion pump configured to draw fluid from the syringe with a negative pressure.

In one preferred and non-limiting embodiment or aspect, the syringe comprises a plunger rod and a syringe barrel, wherein the syringe barrel extends between a proximal end and a distal end, wherein the proximal end of the syringe barrel is configured to receive a distal end of the plunger rod, and wherein the distal end of the syringe barrel is connected to the infusion pump via a fluid line.

In one preferred and non-limiting embodiment or aspect, the vibrator receives a supply of power from the infusion pump.

In one preferred and non-limiting embodiment or aspect, during fluid draw from the syringe by the infusion pump, the vibrator is configured to vibrate one of continuously and periodically.

In one preferred and non-limiting embodiment or aspect, the syringe assembly further comprises at least one pressure sensor configured to determine a vacuum pressure during fluid draw from the syringe by the infusion pump, wherein the vibrator is configured to vibrate based on the determined vacuum pressure.

In one preferred and non-limiting embodiment or aspect, the vibrator is connected to a housing of the infusion pump via a line.

Other preferred and non-limiting embodiment or aspects of the present invention will be set forth in the following numbered clauses:

Clause 1. A syringe assembly, comprising: a syringe; and a vibrator configured to vibrate at at least one frequency, wherein the vibrator is attached to the syringe.

Clause 2. The syringe assembly of clause 1, wherein the vibrator comprises one of an eccentric weight on a motor shaft, a piezoelectric drive, and an inductive drive.

Clause 3. The syringe assembly of clause 1 or 2, wherein the vibrator is configured to vibrate at a natural frequency of the syringe assembly.

Clause 4. The syringe assembly of any of clauses 1-3, wherein the vibrator is configured to vibrate at a plurality of different frequencies.

Clause 5. The syringe assembly of any of clauses 1-4, further comprising: at least one sensor configured to determine a natural frequency of the syringe assembly.

Clause 6. The syringe assembly of any of clauses 1-5, wherein the at least one sensor is configured to determine a dynamic response of the syringe assembly to the plurality of different frequencies and determine the natural frequency of the syringe assembly based on the dynamic response of the syringe assembly to the plurality of different frequencies.

Clause 7. The syringe assembly of any of clauses 1-6, wherein the at least one sensor comprises an accelerometer.

Clause 8. The syringe assembly of any of clauses 1-7, wherein the vibrator is configured to vibrate at the natural frequency of the syringe assembly determined by the at least one sensor.

Clause 9. The syringe assembly of any of clauses 1-8, wherein the vibrator has a predetermined mass configured to tune the natural frequency of the syringe assembly to a preselected natural frequency.

Clause 10. The syringe assembly of any of clauses 1-9, wherein the syringe comprises a plunger rod and a syringe barrel, and wherein the vibrator is attached to the plunger rod.

Clause 11. The syringe assembly of any of clauses 1-10, wherein the syringe barrel extends between a proximal end and a distal end, wherein the proximal end of the syringe barrel is configured to receive a distal end of the plunger rod, and the wherein the vibrator is attached to a proximal end of the plunger rod.

Clause 12. The syringe assembly of any of clauses 1-11, wherein the vibrator is configured to impute motion to the plunger rod in an axial direction of the syringe barrel.

Clause 13. The syringe assembly of any of clauses 1-12, wherein the syringe barrel extends between a proximal end and a distal end, wherein the proximal end of the syringe barrel is configured to receive a distal end of the plunger rod, and wherein the vibrator is attached between a proximal end and the distal end of a plunger rod.

Clause 14. The syringe assembly of any of clauses 1-13, wherein the vibrator is configured to impute motion to the plunger rod in a direction transverse to an axial direction of the syringe barrel.

Clause 15. The syringe assembly of any of clauses 1-14, wherein the syringe comprises a plunger rod and a syringe barrel, and wherein the vibrator is attached to the syringe barrel.

Clause 16. The syringe assembly of any of clauses 1-15, wherein the vibrator is configured to impute motion to the syringe barrel in a direction transverse to an axial direction of the syringe barrel.

Clause 17. The syringe assembly of any of clauses 1-16, wherein the vibrator is removably attached to the syringe.

Clause 18. The syringe assembly of any of clauses 1-17, wherein the vibrator is attached to the syringe by at least one of an adhesive connection, a mechanical connection, and a magnetic connection.

Clause 19. The syringe assembly of any of clauses 1-18, further comprising: an infusion pump configured to draw fluid from the syringe with a negative pressure.

Clause 20. The syringe assembly of any of clauses 1-19, wherein the syringe comprises a plunger rod and a syringe barrel, wherein the syringe barrel extends between a proximal end and a distal end, wherein the proximal end of the syringe barrel is configured to receive a distal end of the plunger rod, and wherein the distal end of the syringe barrel is connected to the infusion pump via a fluid line.

Clause 21. The syringe assembly of any of clauses 1-20, wherein the vibrator receives a supply of power from the infusion pump.

Clause 22. The syringe assembly of any of clauses 1-21, wherein during fluid draw from the syringe by the infusion pump, the vibrator is configured to vibrate one of continuously and periodically.

Clause 23. The syringe assembly of any of clauses 1-22, further comprising: at least one pressure sensor configured to determine a vacuum pressure during fluid draw from the syringe by the infusion pump, wherein the vibrator is configured to vibrate based on the determined vacuum pressure.

Clause 24. The syringe assembly of any of clauses 1-23, wherein the vibrator is connected to a housing of the infusion pump via a line.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWING(S)

FIG. 4A is a graph showing the minimum pressures achieved for each test syringe

FIG. 5 is a block diagram of a syringe assembly according to principles of the present invention;

FIG. 8 is perspective view of a vibrator mounted on a syringe barrel according to principles of the present invention.

DETAILED DESCRIPTION

Figure 1:
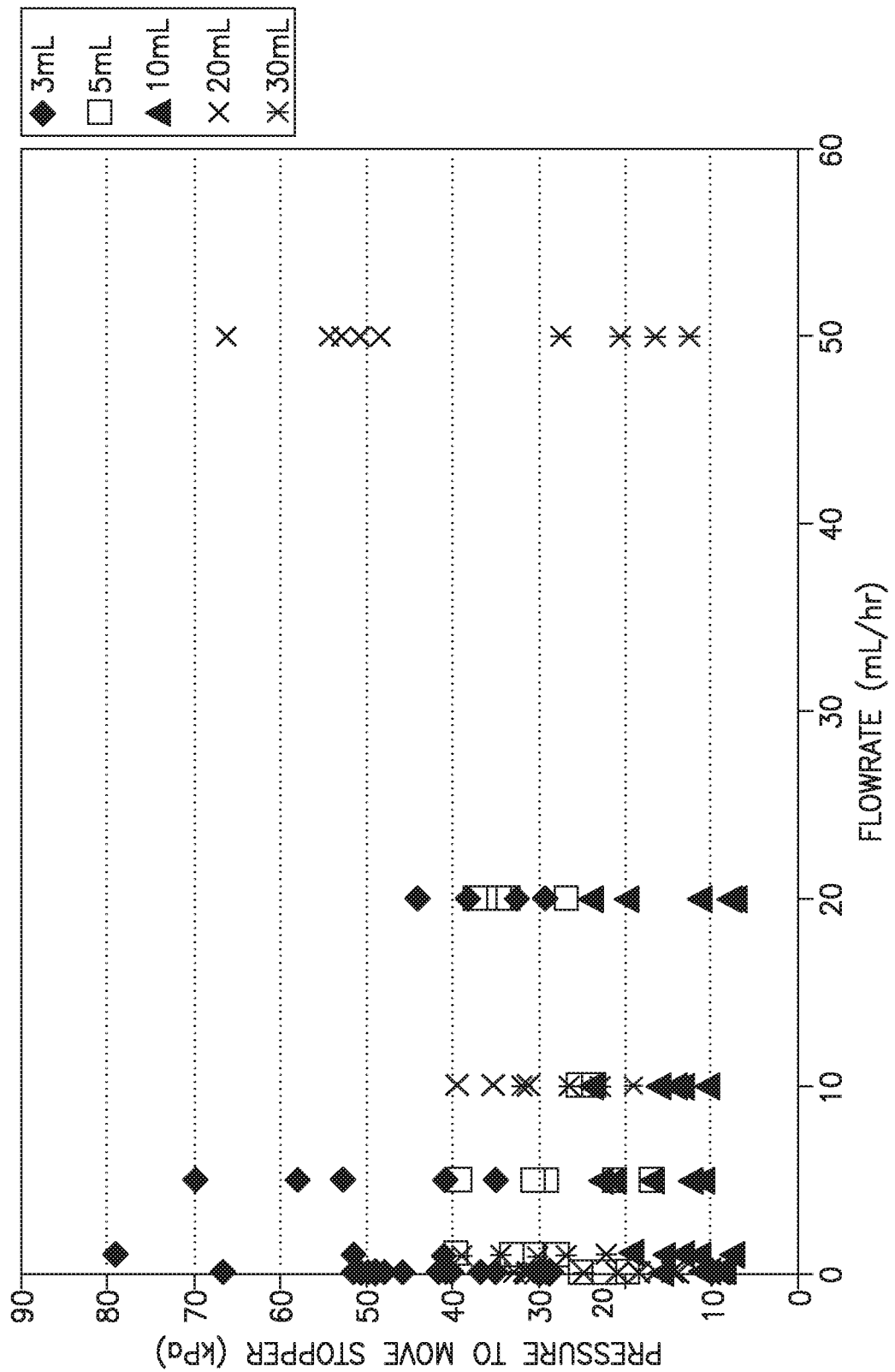
FIG. 1 is a graph showing syringe break-loose force or stiction data for the pressures required to draw from a range of syringe sizes.

For purposes of the description hereinafter, the terms "upper", "lower", "right", "left", "vertical", "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The use of a vibration module attached to a syringe provides a solution to the high stiction (low pressure) problem. Vacuum pressure reductions, for example, of about 30-70% have been demonstrated, and much better performance is expected. For example, if an objective is to induce small-scale cyclic axial motions (micro-dithering) in a syringe plunger, the plunger/rod system can be treated as a classical spring-mass-damper, with a cyclic driving force $F_d$. In this case, Newton's second law yields the 2nd order equation of motion as shown in Equation 1:

$$\ddot{x} + \frac{c}{m}\dot{x} + \frac{k}{m}x = \frac{F_d}{m} \quad (1)$$

where x is the axial coordinate of the syringe plunger, c is the damping coefficient, k is the spring constant, or stiffness of the plunger rod, m is the mass being oscillated, and again, $F_d$ is the cyclic driving force.

This second order ordinary differential equation (ODE) is usually expressed in terms of the damping ratio $\zeta$ and un-damped natural frequency $\omega_n$, as shown in Equation 2:

$$\ddot{x} + 2\zeta\omega_n\dot{x} + \omega_n^2 x = \frac{F_d}{m} \quad (2)$$

where $\omega_n$ and $\zeta$ are respectively defined in Equation 3 and Equation 4:

$$\omega_n = \sqrt{\frac{k}{m}} \quad (3)$$

$$\zeta = \frac{c}{2\sqrt{mk}} \quad (4)$$

Figure 2:
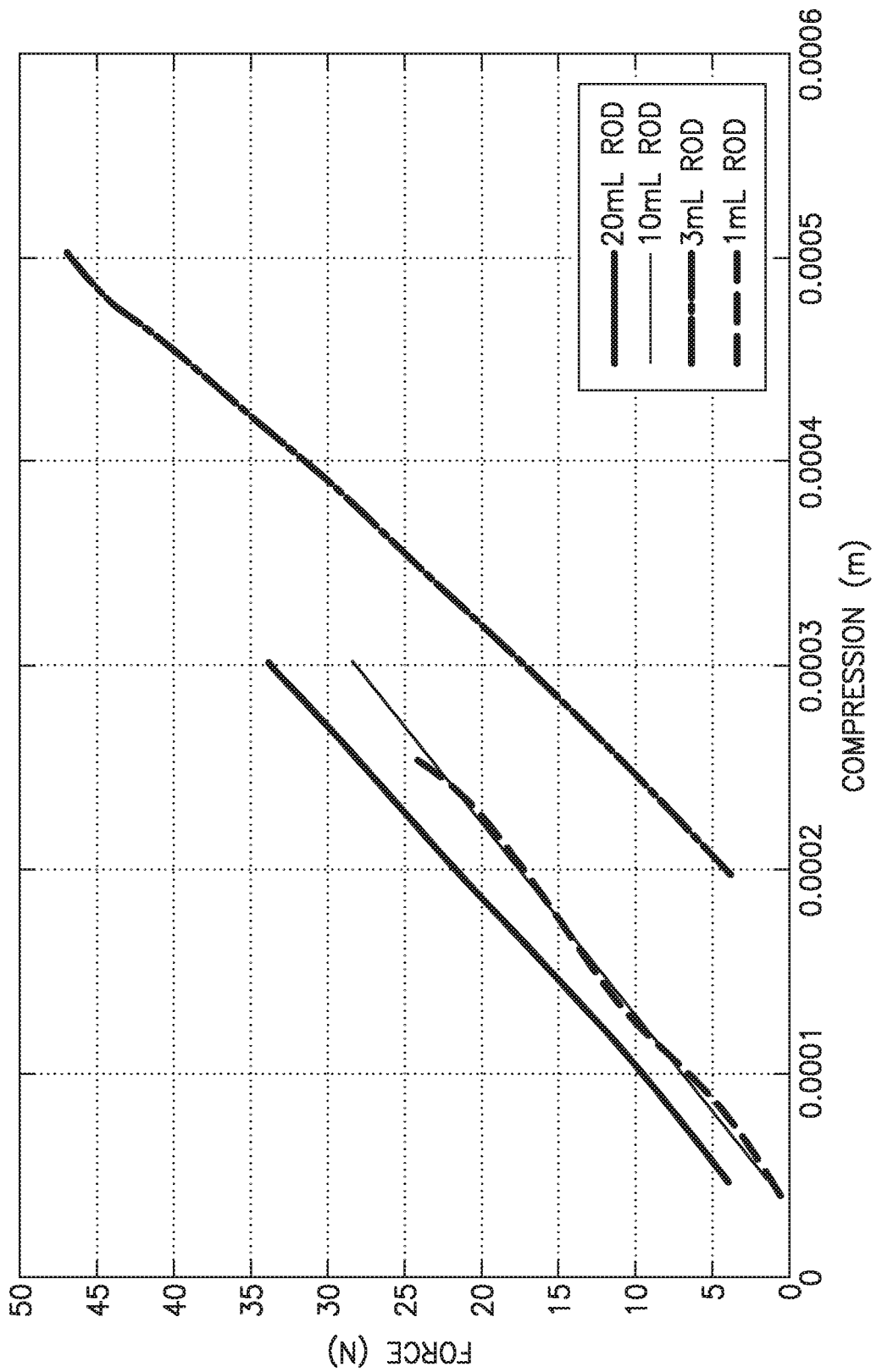
FIG. 2 is a graph showing the first linear portion of the compression curve for four test plunger rods compressed to measure their spring constant during the first small deflection.

The un-damped natural frequency $\omega_n$ may be considered as a primary metric of interest. To maximize transfer of vibrational energy to the stopper, it is desirable to drive the plunger rod at or near the natural frequency of the system. FIG. 2 illustrates the first linear portion of the compression curve for four example plunger rods compressed between anvils in an Instron machine to measure their spring constant during the first small deflection. These curves, together with the mass of each rod/plunger pair can be used to calculate the natural frequency of each of the four test syringe sizes, as shown in the following Table 1. Although not included in the example results shown in Table 1, it is noted that the real mass of interest can include some or all of the fluid mass in the syringe, and may substantially decrease these natural frequencies.

TABLE 1

| Syringe | 1 mL | 3 mL | 10 mL | 20 mL |
| --- | --- | --- | --- | --- |
| Mass (kg) | 1.09E−03 | 1.14E−03 | 3.62E−03 | 6.28E−03 |
| K (n/m) | 108251 | 143409 | 106488 | 119265 |
| ωn (rad/s) | 9957.365 | 11231.72 | 5420.187 | 4356.368 |
| ωn (Hz) | 1584.764 | 1787.583 | 862.6496 | 693.3376 |

Figure 3A:
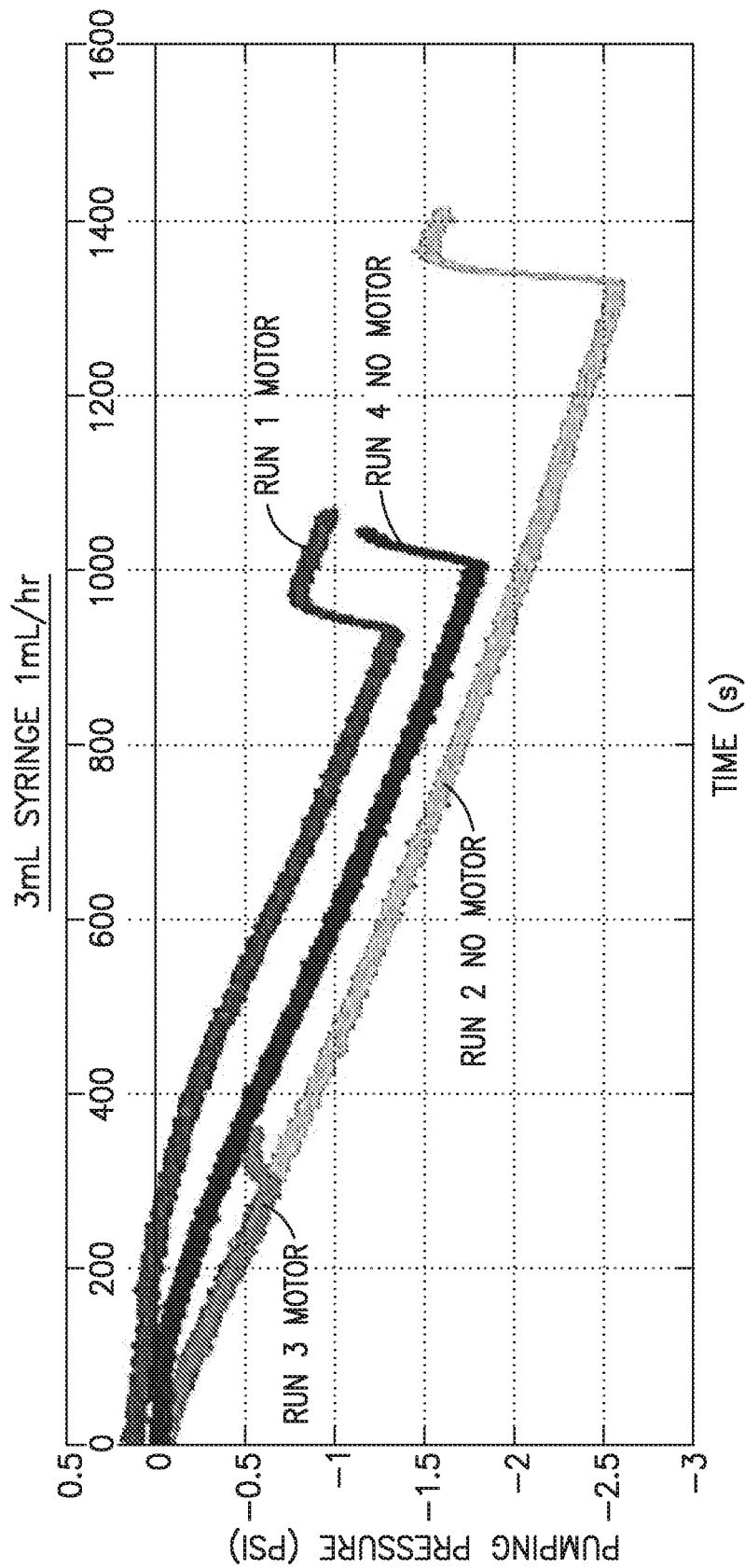
FIG. 3A is a graph showing raw pressure traces over time for a 3 mL test syringe.
Figure 3B:
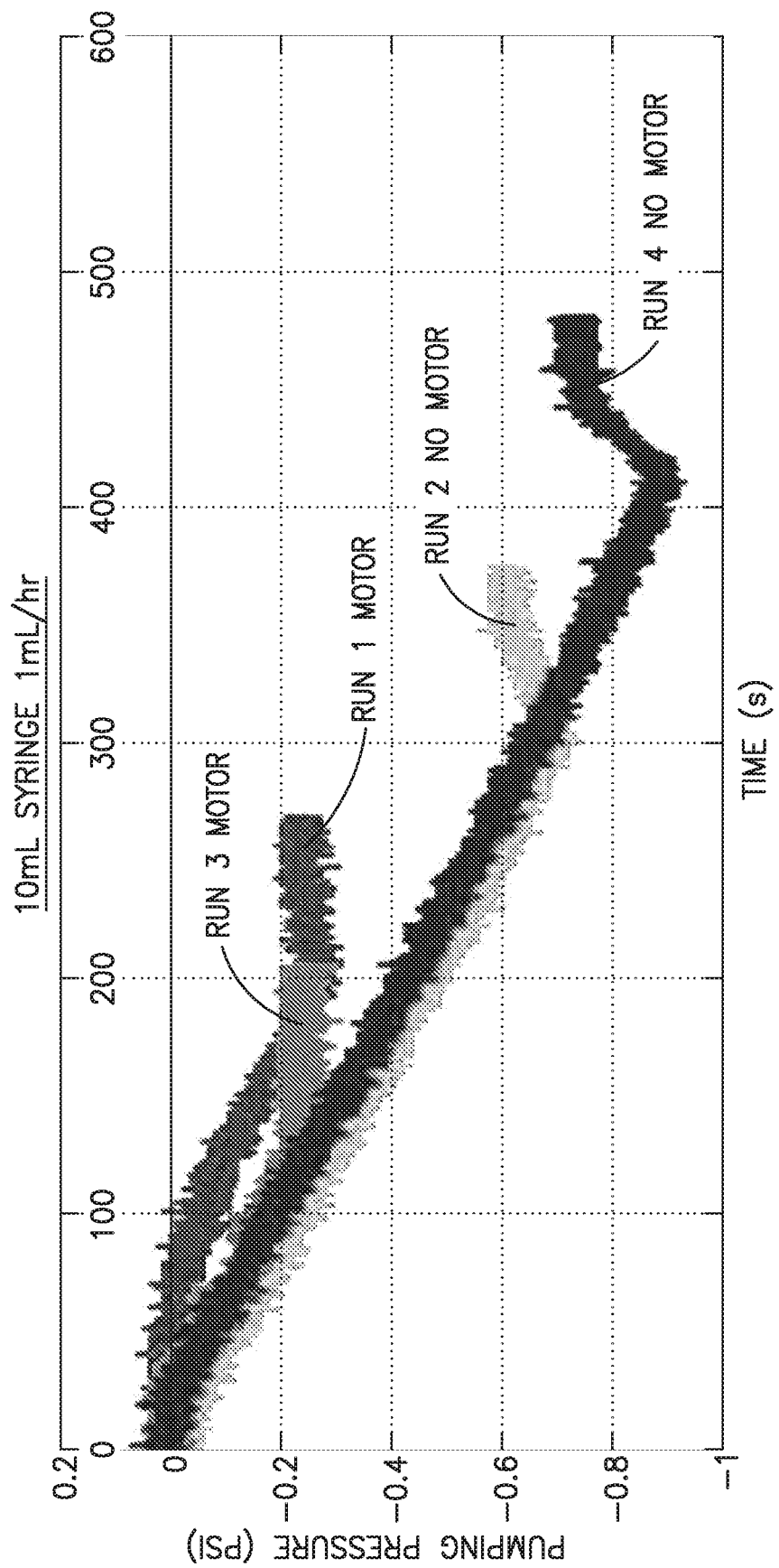
FIG. 3B is a graph showing raw pressure traces over time for a 10 mL test syringe.
Figure 3C:
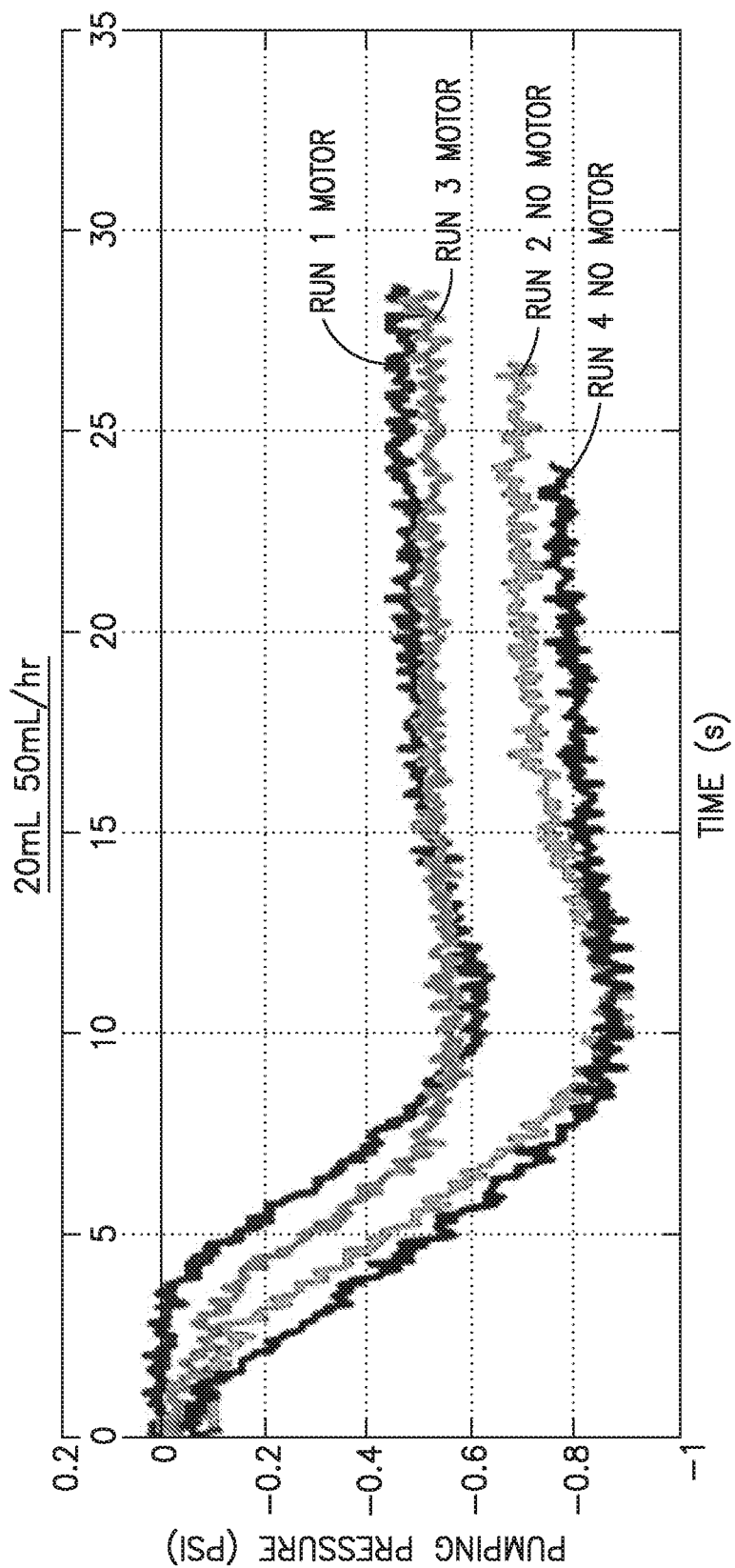
FIG. 3C is a graph showing raw pressure traces over time for a 20 mL test syringe.

FIGS. 3A-C illustrate raw pressure traces over time for a 3 mL test syringe, a 10 mL test syringe, and a 20 mL test syringe, respectively, during an example test in which a syringe pump was plumbed to draw from the test syringes at flow rates selected to produce maximum stiction. A vibrator motor was affixed to the end of the plunger rod of each syringe with the motor axis perpendicular to the syringe axis. Each of the 3 test syringes were subjected to four test runs in an A-B-A-B-style (motor, no-motor, motor, no-motor) sequence. When used, the motor was tuned to vibrate at a frequency substantially equal to the vibration frequency of the syringe system including the syringe and the vibration motor. Each syringe was left undisturbed for about five minutes prior to each test run. Each test run continued, and the pressure-trace was recorded up until the first "break-loose" event.

Figure 4B:
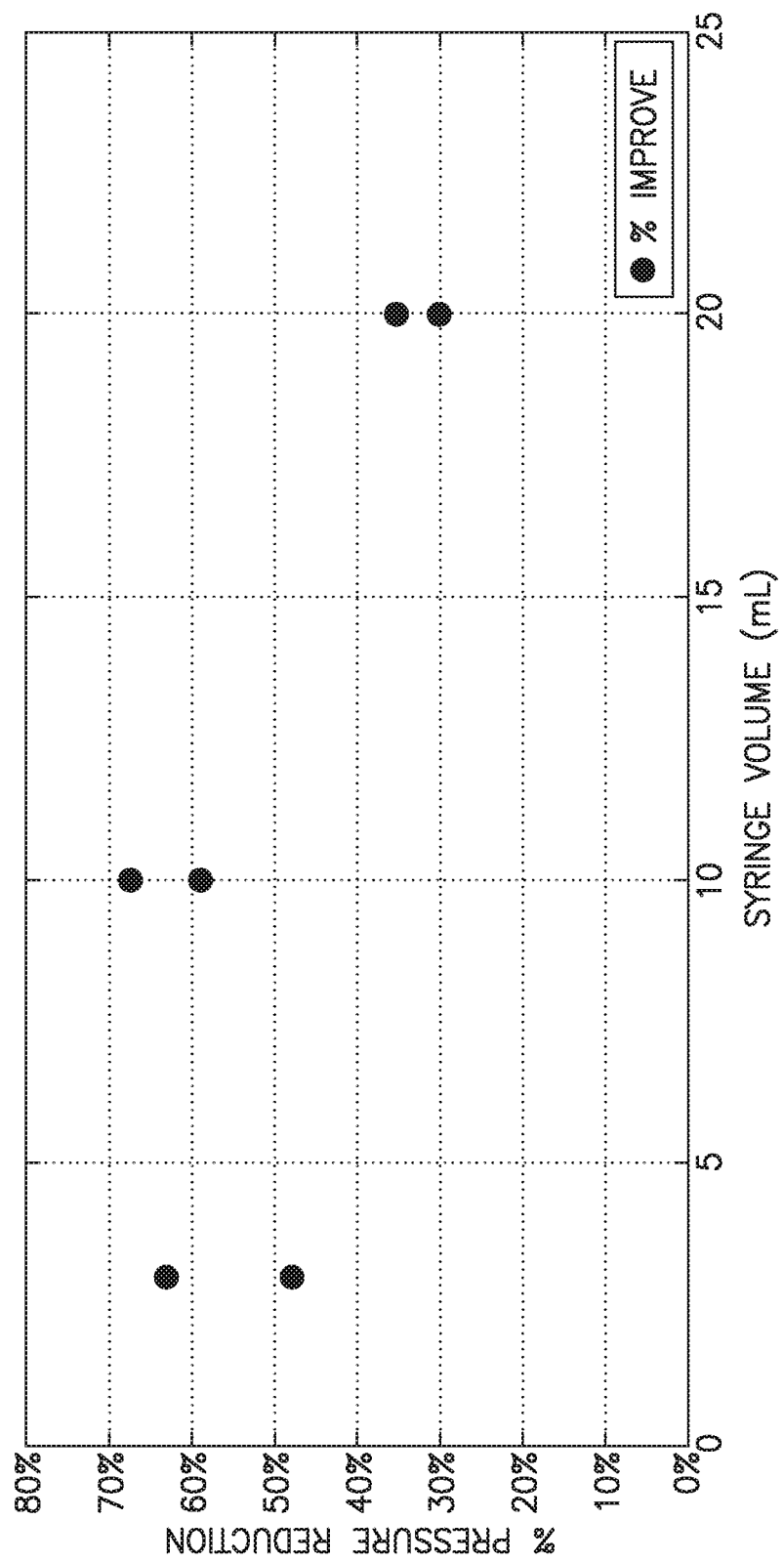
FIG. 4B is a graph showing the percent improvement of vibration motor runs for each test syringe.

FIGS. 4A and 4B respectively summarize the minimum pressures achieved for each test run and the percent improvement for the vibration motor runs. Pressure reductions of 30-70% during fluid draw were demonstrated with the vibration motor, as well as the ability of a vibrator to break the stiction of the occasional worst-case syringe.

Referring now to FIG. 5, a syringe assembly 10 according to preferred and non-limiting embodiments or aspects comprises a syringe 100 and a vibrator 150 configured to vibrate at at least one frequency. The vibrator 150 is attached to the syringe 100. The syringe assembly 10 may further comprise an infusion pump 170 configured to draw fluid from the syringe 100 with a negative pressure via a fluid line 180. The syringe 100 comprises a plunger rod. 102 and a syringe barrel 104 that extends between a proximal end 104a and a distal end 104b. The proximal end 104a of the syringe barrel 104 includes an opening 105 configured to receive a distal end 102b of the plunger rod 102 including a stopper 107. The distal end 104a of the syringe barrel 104 can be connected to the infusion pump 170 via the fluid line 180 for fluid draw from the syringe 100 by the infusion pump 170. In another example, the distal end 104a of the syringe barrel 104 may comprise a needle cannula for fluid transfer from the syringe 100 in response to compression of the plunger rod 102.

The vibrator 150 may include one of an eccentric weight on a motor shaft, a piezoelectric drive, and an inductive drive. The vibrator 150 may receive a supply of power from the infusion pump 170, another external power supply, or an internal battery (not shown). The vibrator can be configured to vibrate at any frequency including ultrasonic frequencies and lower frequencies. In some examples the vibrator 150 can include a controller including a processor and memory configured to control operation of the vibrator 150. In another example, the vibrator 150 can be connected to an external controller via a wired or wireless connection to control operation of the vibrator 150. In one implementation, the infusion pump 170 may include the external controller to control operation of the vibrator 150. For example, the controller can control the vibrator to start or stop vibration, a frequency at which the vibrator vibrates, and/or a period or whether the vibrator 150 vibrates continuously, periodically, or based on sensor feedback as described in more detail herein. It is contemplated herein that the vibrator 150 could be rotational, linear uniaxial, or multiaxial. It is further contemplated herein that the vibrator 150 can include piezoelectric, inductive or other actuation technology.

Figure 6:
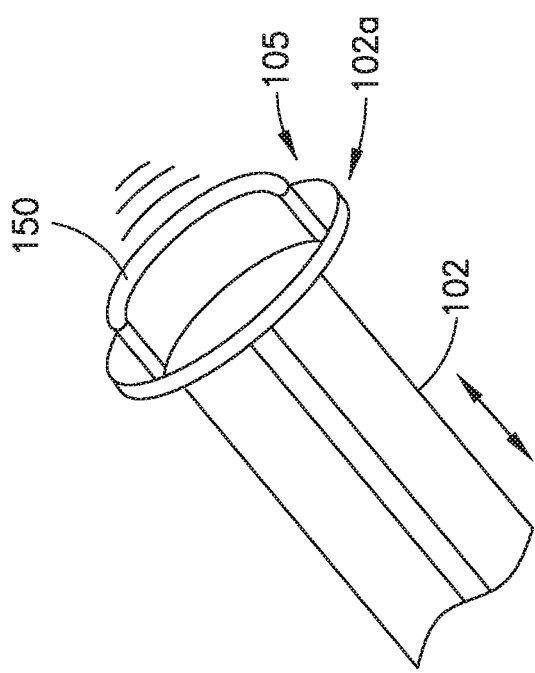
FIG. 6 is a perspective view of a vibrator mounted on the proximal end of a plunger rod according to principles of the present invention.

In one example, the vibrator 150 can be attached to the plunger rod 102. For example, the vibrator 150 can be attached to the proximal end 102a of the plunger rod 102 as shown in FIG. 6, e.g., on top of a finger flange or disc at the proximal end 102a of the plunger rod 102. The vibrator can be configured to impute motion to the plunger rod 102 in an axial direction of the syringe barrel 104 and/or the plunger rod 102. For example, the vibrator 150 may be configured to vibrate back-and-forth in the proximal and distal directions of the syringe to impute motion in the axial direction thereof.

Figure 7:
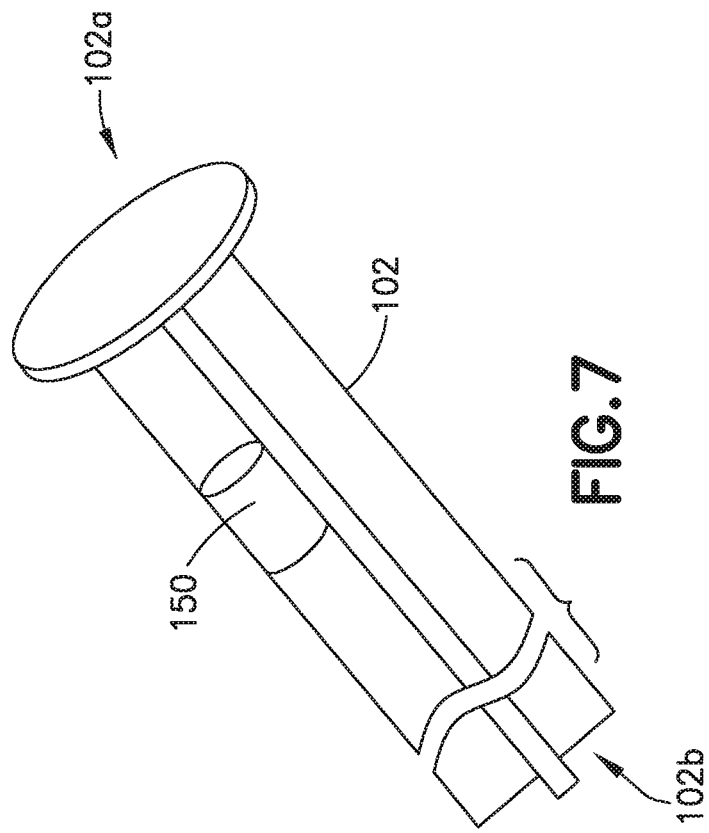
FIG. 7 is a perspective view of a vibrator mounted on the shaft of a plunger rod according to principles of the present invention.

In another example, the vibrator 150 can be attached between the proximal end 102a and the distal end 102b of the plunger rod 102 as shown in FIG. 7, e.g., along or within the shaft of the plunger rod 102 and/or between cross-shaped cross sections thereof. In still another implementation, the vibrator 150 can be attached to the syringe barrel 104 as shown in FIG. 8, e.g., to an outer surface of the syringe barrel 104 between the proximal end 104a and the distal end 104b of the syringe barrel 104. The vibrator 150 can be configured to impute motion to the plunger rod 102 and/or the syringe barrel 104 in a direction transverse to the axial direction of the syringe barrel 104 and/or the plunger rod 102. For example, when attached to the syringe barrel, the vibrator 150 may be configured to vibrate back-and-forth in a direction transverse to the axial direction of the syringe 100. It is noted herein that the vibrator 150 can be secured to any portion of the plunger rod 102, or a portion of the syringe barrel 104, as long as the vibrator is configured to impute axial motion to the syringe assembly.

The vibrator 150 may be removably attached to the syringe 100. For example, the vibrator 150 can be attached to the syringe by at least one of an adhesive connection, a mechanical connection, and a magnetic connection. An adhesive connection may comprise a permanent or removable and reusable adhesive pad on the vibrator 150 that forms an adhesive connection between the vibrator 150 and the syringe 100. A mechanical connection may comprise a band or clip configured to secure the vibrator 150 to the syringe barrel 104 or the plunger rod 102. A magnetic connection may comprise a magnet on each of the vibrator 150 and the syringe barrel 104 or plunger rod 102 to secure the vibrator 150 to the syringe 100.

In one example, the vibrator 150 can be configured to vibrate at a natural frequency of a particular syringe 100, the syringe assembly 10, or a syringe system including the syringe 100 and the vibrator 150 itself. In another example, the vibrator 150 can be configured to vibrate at a plurality of different frequencies. The syringe assembly 10 may comprise at least one sensor 190, e.g., an accelerometer, configured to determine a natural frequency of the syringe 100, the syringe assembly 10, or a syringe system including the syringe 100 and the vibrator 150. The at least one sensor 190 can be connected to the vibrator 150 and/or the controller for the vibrator 150. In one configuration, the sensor 190 can include an accelerometer. For example, the at least one sensor 190 can be configured to determine a dynamic response of the syringe assembly 10 to the plurality of different frequencies and determine the natural frequency of the syringe assembly 10 based on the dynamic response of the syringe assembly 10 to the plurality of different frequencies. For example, when the frequency at which the vibrator 150 is vibrating is equal to the natural frequency of the syringe assembly 10, the amplitude of vibration increases exponentially, which is known as resonance. The at least one sensor 190 and/or the controller for the vibrator 150 can determine the frequency at which the syringe assembly 10 achieves maximum amplitude of vibration, i.e., resonance, and control the vibrator 150 to vibrate at the determined natural frequency during fluid draw from the syringe 100. The vibrator 150 can be configured to vibrate at the natural frequency of the syringe assembly 10 determined by the at least one sensor 190.

In some implementations, the vibrator 150 has a predetermined mass configured to tune the natural frequency of the syringe assembly 10 to a preselected natural frequency. For example, the mass of the vibrator 150 can be designed to tune the natural frequency of the system including the syringe 100 and the vibrator 150 itself to a more desirable value, such as a preprogrammed vibration frequency of the vibrator 150.

The vibrator 150 can be configured and/or controlled to vibrate one of continuously and periodically. For example, during fluid draw from the syringe 100 by the infusion pump 170, the vibrator 150 may vibrate one of continuously and periodically at the natural frequency of the syringe assembly 10. In another implementation, the syringe assembly 10 may further comprise at least one pressure sensor 195 configured to determine a vacuum pressure during fluid draw from the syringe 100 by the infusion pump 170. The at least one pressure sensor 195 may be located along and/or within the fluid line 180 connecting the infusion pump 170 to the syringe 100 to draw the fluid from the syringe 100. The at least one pressure sensor 195 can be connected to the vibrator 150 and/or the controller of the vibrator 150, and the vibrator 150 can be configured or controlled to vibrate based on the level of negative pressure determined by the at least one pressure sensor 195. For example, if the determined negative pressure violates a threshold pressure level, e.g., indicating a high stiction, the controller can control the vibrator 150 to vibrate based on the violated threshold to help reduce the stiction and the negative pressure required to continue fluid draw by the infusion pump 170. In operation, when pressure in the pump reaches a threshold pressure, the vibrator 150 may turn on thereby breaking the stiction and reducing the negative pressure in the syringe, and allow the pump to continue. In one example, the vibrator 150 may only need to be turned on periodically to keep the negative pressure above the set threshold.

Figure 9:
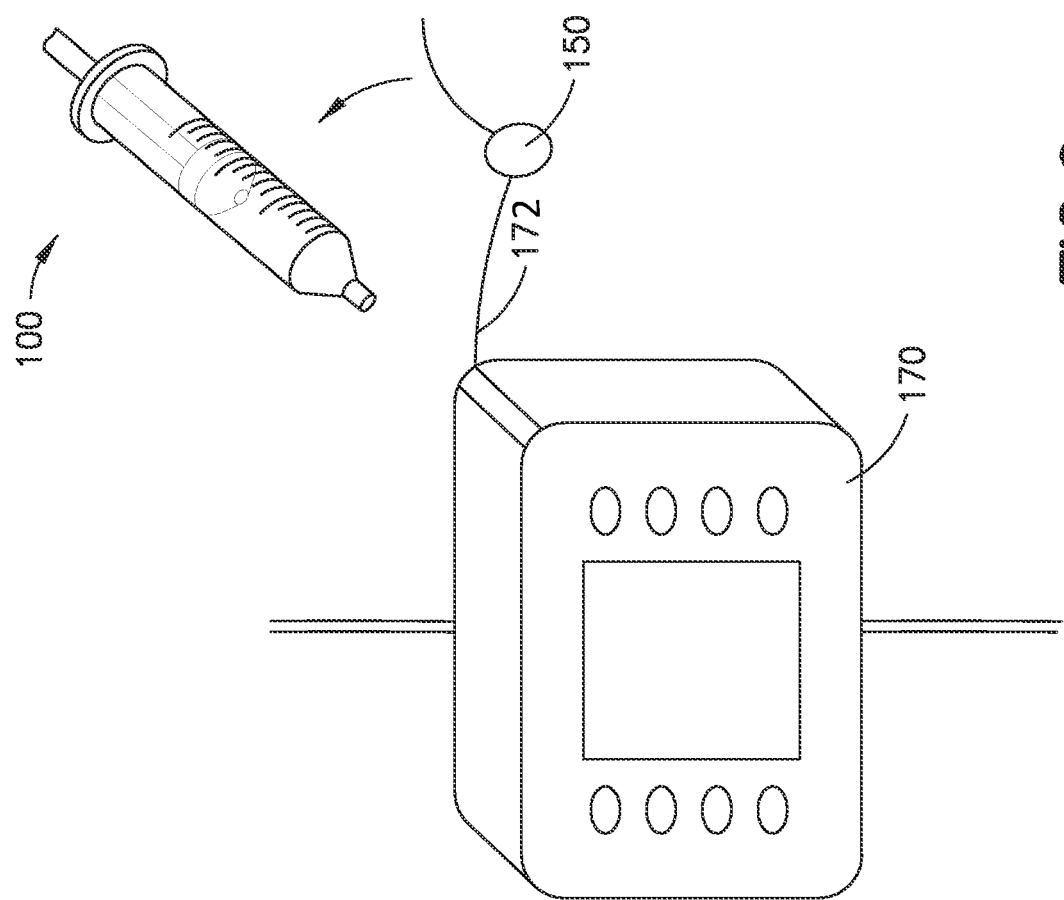
FIG. 9 is a perspective view of a vibrator connected to an infusion pump according to principles of the present invention.

In one example, as shown in FIG. 9, the vibrator 150 is connected to a housing of the infusion pump 170 via a line 172, such as a string or dongle, which can reduce occurrences of lost vibrators 150 in the case of a reusable vibrator 150 to be used with multiple different syringes 100 at the same infusion pump 170.

Although the invention has been described in detail for the purpose of illustration based on what is currently considered to be the most practical and preferred embodiments or aspects, it is to be understood that such detail is solely for that purpose and that the invention is not limited to the disclosed embodiments or aspects, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A syringe assembly, comprising:
   a syringe including a plunger rod and a syringe barrel;
   a vibrator configured to vibrate at a plurality of different frequencies, wherein the vibrator is attached to one of the plunger rod and the syringe barrel of the syringe;
   at least one sensor configured to determine a dynamic response of the syringe assembly to the plurality of different frequencies and determine a natural frequency of the syringe assembly based on the dynamic response of the syringe assembly to the plurality of different frequencies; and
   a controller configured to control the vibrator to vibrate at the determined natural frequency of the syringe assembly during fluid draw from the syringe.

2. The syringe assembly of claim 1, wherein the vibrator comprises one of an eccentric weight on a motor shaft, a piezoelectric drive, and an inductive drive.

3. The syringe assembly of claim 1, wherein the at least one sensor comprises an accelerometer.

4. The syringe assembly of claim 1, wherein the vibrator has a predetermined mass configured to tune the natural frequency of the syringe assembly to a preselected natural frequency.

5. The syringe assembly of claim 1, wherein the vibrator is attached to the plunger rod.

6. The syringe assembly of claim 5, wherein the syringe barrel extends between a proximal end and a distal end, wherein the proximal end of the syringe barrel is configured to receive a distal end of the plunger rod, and the wherein the vibrator is attached to a proximal end of the plunger rod.

7. The syringe assembly of claim 6, wherein the vibrator is configured to impute motion to the plunger rod in an axial direction of the syringe barrel.

8. The syringe assembly of claim 5, wherein the syringe barrel extends between a proximal end and a distal end, wherein the proximal end of the syringe barrel is configured to receive a distal end of the plunger rod, and wherein the vibrator is attached between a proximal end and the distal end of a plunger rod.

9. The syringe assembly of claim 8, wherein the vibrator is configured to impute motion to the plunger rod in a direction transverse to an axial direction of the syringe barrel.

10. The syringe assembly of claim 1, wherein the vibrator is attached to the syringe barrel.

11. The syringe assembly of claim 10, wherein the vibrator is configured to impute motion to the syringe barrel in a direction transverse to an axial direction of the syringe barrel.

12. The syringe assembly of claim 1, wherein the vibrator is removably attached to the syringe.

13. The syringe assembly of claim 1, wherein the vibrator is attached to the syringe by at least one of an adhesive connection, a mechanical connection, and a magnetic connection.

14. The syringe assembly of claim 1, further comprising:
   an infusion pump configured to draw fluid from the syringe with a negative pressure.

15. The syringe assembly of claim 14, wherein the syringe comprises a plunger rod and a syringe barrel, wherein the syringe barrel extends between a proximal end and a distal end, wherein the proximal end of the syringe barrel is configured to receive a distal end of the plunger rod, and wherein the distal end of the syringe barrel is connected to the infusion pump via a fluid line.

16. The syringe assembly of claim 15, further comprising:
   at least one pressure sensor configured to determine a vacuum pressure during fluid draw from the syringe by the infusion pump, wherein the vibrator is configured to vibrate based on the determined vacuum pressure.

17. The syringe assembly of claim 14, wherein the vibrator receives a supply of power from the infusion pump.

18. The syringe assembly of claim 14, wherein during fluid draw from the syringe by the infusion pump, the vibrator is configured to vibrate one of continuously and periodically.

19. The syringe assembly of claim 14, wherein the vibrator is connected to a housing of the infusion pump via a line.

20. A method, comprising:
   providing a syringe assembly including a plunger rod, a syringe barrel, and a vibrator configured to vibrate at a plurality of different frequencies, wherein the vibrator is attached to one of the plunger rod and the syringe barrel of the syringe assembly;
   vibrating, with the vibrator, the syringe assembly at a plurality of different frequencies;
   determining, with a sensor, a dynamic response of the syringe assembly based on the plurality of different frequencies;
   determining with the sensor, a natural frequency of the syringe assembly based on the dynamic response of the syringe assembly; and
   providing a controller configured to control the vibrator to vibrate at the determined natural frequency of the syringe assembly.

21. The method of claim 20, wherein the controller is configured to control the vibrator to vibrate at the determined natural frequency of the syringe assembly during a fluid draw procedure.

22. The method of claim 20, wherein the sensor that determines the dynamic response of the syringe assembly and the sensor that determines the natural frequency of the syringe assembly are different sensors.

23. The method of claim 20, wherein the sensor that determines the dynamic response of the syringe assembly and the sensor that determines the natural frequency of the syringe assembly is the same sensor.

\* \* \* \* \*